(12) United States Patent
Kim et al.

(10) Patent No.: US 8,173,607 B2
(45) Date of Patent: May 8, 2012

(54) PROMOTER FOR THE PRODUCTION OF HYALURONIC ACID CONTAINING GINSENOSIDE COMPOUND K

(75) Inventors: Su-Jong Kim, Yongin-si (KR);
Byung-Young Kang, Seoul (KR);
Si-Young Cho, Yongin-si (KR);
Hui-Kyoung Chang, Yongin-si (KR);
Dae-Seok Sung, Seoul (KR); Myeong Hoon Yeom, Yongin-si (KR);
Kwang-Sik Woe, Chungju-si (KR);
Duck-Hee Kim, Seoul (KR); Han-Kon Kim, Suwon-si (KR); Young-Chul Sim, Seongnam-si (KR); Hak-Hee Kang, Seongnam-si (KR); Yong-Sung Lee, Seoul (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 12/184,622

(22) Filed: Aug. 1, 2008

(65) Prior Publication Data

US 2009/0062217 A1 Mar. 5, 2009

Related U.S. Application Data

(63) Continuation of application No. 10/539,011, filed as application No. PCT/KR03/01889 on Sep. 16, 2003, now abandoned.

(30) Foreign Application Priority Data

Dec. 26, 2002 (KR) .......................... 10-2002-084036

(51) Int. Cl.
*A61K 31/704* (2006.01)
*A61K 31/70* (2006.01)
(52) U.S. Cl. .................. 514/26; 514/25; 536/5; 536/4.1
(58) Field of Classification Search .................... 514/26, 514/25; 536/5, 4.1
See application file for complete search history.

(56) References Cited

U.S. PATENT DOCUMENTS 5,955,083 A 9/1999 Bonte et al.

FOREIGN PATENT DOCUMENTS

| | | | |
|---|---|---|---|
| EP | 1213026 A1 | 6/2002 | |
| EP | 1327434 A1 * | 7/2003 | |
| JP | 2003-212776 A | 7/2003 | |
| JP | 2003-238424 A | 8/2003 | |
| KR | 2003-60017 A | 7/2003 | |
| KR | 2003-60018 A | 7/2003 | |
| KR | 2003-65273 A | 8/2003 | |
| KR | 2003-80429 | 10/2003 | |
| WO | 97/31013 A1 | 8/1997 | |
| WO | 99/07338 A1 | 2/1999 | |
| WO | 02/067950 A1 | 9/2002 | |

OTHER PUBLICATIONS

Tanaka et al. (Fragrance Journal (1991), 19(8), 90-2)(abstract sent).*
Hasegawa et al. (Planta Medica 62 (1996) 453-457).*
Lee, S.J., et al., "Induction of apoptosis by a novel intestinal metabolite of ginseng saponin via cytochrome c-mediated activation of caspase-3 protease," Biochemical Pharmacology, vol. 60(5), (2000), 677-685.
Hideo, Kasegawa, "Metabolic activation of ginsenoside agains cancer: intestinal bacterial deglycosylation and hapatic fatty-acid esterification," Wakan Iyakugaku Zasshi, vol. 18(6), (2000), 218-278.
Longas, Maria O., et al., "Evidence for Structural Changes in Dermatan Sulfate and Hyaluronic Acid with Aging," Carbohydrate Research, vol. 159, 1987, pp. 127-136.
Ghersetich, Ilaria, et al., "Hyaluronic Acid in Cutaneous Intrinsic Aging," International Journal of Dermatology, vol. 33, No. 2, Feb. 1994, pp. 119-122.
Heldin, Paraskevi, et al., "Effect of growth factors on hyaluronan synthesis in cultured human fibroblasts," Biochem. J., vol. 258, 1989, pp. 919-922.
Heldin, Paraskevi, et al., "Characterization of the molecular mechanism involved in the activation of hyaluronan synthetase by platelet-derived growth factor in human mesothelial cells," Biochem. J., vol. 283, 1992, pp. 165-170.
Suzuki, Masanobu, et al., "Stimulation of hyaluronan biosynthesis by platelet-derived growth factor-BB and transforming growth factor-β1 involves activation of protein kinase C," Biochem. J., vol. 307, 1995, pp. 817-821.
Tirone, Evelina, et al., "Hyaluronan Synthesis by Mouse Cumulus Cells Is Regulated by Interactions between Follicle-stimulating Hormone (or Epidermal Growth Factor) and a soluble Oocyte Factor (or Transforming Growth Factor beta1)," The Journal of Biological Chemistry, vol. 272, No. 8, Feb. 21, 1997, pp. 4787-4794.
Tammi, Raija, et al., "Hyaluronate Accumulation in Human Epidermis Treated with Retinoic Acid in Skin Organ Culture," The Journal of Investigative Dermatology, vol. 92, No. 3, Mar. 1989, pp. 326-332.
Akiyama, Hiroshi, et al., "Analytical Studies on Hyaluronic Acid Synthesis by Normal Human Epidermal Keratinocytes Cultured in a Serum-Free Medium," Biol. Pharm. Bull., vol. 17, No. 3, 1994, pp. 361-264.
Sakai, Shingo, et al., "N-Methyl-L-Serine Stimulates Hyaluronan Production in Human Skin Fibroblasts," Skin Pharmacol. Appl. Skin Physiol., vol. 12, 1999, pp. 276-283.
Sobel, Harry, et al., "Effect of Estradiol on Hyaluronic Acid in the Skin of Aging Mice," Steroids, vol. 16, No. 1, Jul. 1970, pp. 1-3.
Beltley, J. Peter, et al., "Increased Hyaluronate and Collagen Biosynthesis and Fibroblast Estrogen Receptors in Macaque Sex Skin," The Journal of Investigative Dermatology, vol. 87, No. 5, Nov. 1986, pp. 668-673.

(Continued)

*Primary Examiner* — Shaojia Anna Jiang
*Assistant Examiner* — Michael C Henry
(74) *Attorney, Agent, or Firm* — Sughrue Mion, PLLC

(57) ABSTRACT

There are provided a promoter containing ginsenoside compound K for the production of hyaluronic acid, and more particularly, a new efficacy of 20-O-β-D-glucopyranosyl-20 (S)-protopanaxadiol (compound K), a chief metabolite of ginseng saponin, to increase the expression of hyaluronic acid synthase gene in human cell and thereby to promote the production of hyaluronic acid, and an anti-aging agent containing the promoter for the production of hyaluronic acid as an effective ingredient.

2 Claims, 5 Drawing Sheets

OTHER PUBLICATIONS

Miyazaki, Kouji, et al., "Genistein and Daidzein Stimulate Hyaluronic Acid Production in Transformed Human Keratinocyte Culture and Hairless Mouse Skin," Skin Pharmacol. Appl. Skin Physiol., vol. 15, 2002, pp. 175-183.

Weigel, Paul H., et al., "Hyaluronan Synthases," The Journal of Biological Chemistry, vol. 272, No. 22, May 30, 1997, pp. 13997-14000.

Pienimaki, Juha-Pekka, et al., "Epidermal Growth Factor Activates Hyaluronan Synthase 2 in Epidermal Keratinocytes and Increases Pericellular and Intracellular Hyaluronan," The Journal of Biological Chemistry, vol. 276, No. 23, Jun. 8, 2001, pp. 20428-20435.

Hasegawa, Hideo, et al., "Main Ginseng Saponin Metabolites Formed by Intestinal Bacteria," Planta Med., vol. 62, 1996, pp. 453-457.

Karikura, M., et al., "Studies on Absorption, Distribution, Excretion and Metabolism of Ginseng Saponins. V. The Decomposition Products of Ginsenoside Rb2 in the Large Intestine of Rats," Chem. Pharm. Bull., vol. 38, No. 10, 1990, pp. 2859-2861.

Fleischmajer, Raul, et al., "Human Dermal Glycosaminoglycans and Aging," Biochimica et Biophysica Acta, vol. 279, 1972, pp. 265-275.

Abstract of IL HWA CO., LTD. KR 2003-0065273, Aug. 6 2003.

Japanese Office Action issued in JP application No. 10-2004-562980 on Feb. 16, 2010, with an English language translation.

European Search Report dated Apr. 22, 2010, issued in European Patent Application No. 03813984.6-1216/1575982.

Kim, Dong-Hyun, "Herbal Medicines Are Activated by Intestinal Microflora", Natural Product Sciences, Jun. 2002, pp. 35-43, vol. 8, No. 2.

Tanaka, Hiroshi et al, "Effect of panax ginseng on the production of glycosaminoglycans in cultured human skin fibroblast", Fragrance Journal, Jan. 1, 1991, pp. 90-92, vol. 28, No. 1, Tokyo, Japan.

Court, William E., "The Pharmacology and Therapeutics of Ginseng", Ginseng the Genus Panax in Medicinal and Aromatic Plants: Industrial Profiles, 2000, pp. 117-198, vol. 15, Harwood Academic Publishers.

* cited by examiner a b

HAS1

HAS2

HAS3

GAPDH

SM    0H    24H    48H

SEQUENCE LISTING

<160> NUMBER OF SEQ ID NOS: 6

<210> SEQ ID NO 1
<211> LENGTH: 25
<212> TYPE: DNA
<213> ORGANISM: Artificial Sequence
<220> FEATURE:
<223> OTHER INFORMATION: PCR amplification primer

<400> SEQUENCE: 1
accatcgcct tcgccctgct catcc                                              25

<210> SEQ ID NO 2
<211> LENGTH: 25
<212> TYPE: DNA
<213> ORGANISM: Artificial Sequence
<220> FEATURE:
<223> OTHER INFORMATION: PCR amplification primer

<400> SEQUENCE: 2
cccgctccac attgaaggct accca                                              25

<210> SEQ ID NO 3
<211> LENGTH: 30
<212> TYPE: DNA
<213> ORGANISM: Artificial Sequence
<220> FEATURE:
<223> OTHER INFORMATION: PCR amplification primer

<400> SEQUENCE: 3
tttctttatg tgactcatct gtctcaccgg                                         30

<210> SEQ ID NO 4
<211> LENGTH: 28
<212> TYPE: DNA
<213> ORGANISM: Artificial Sequence
<220> FEATURE:
<223> OTHER INFORMATION: PCR amplification primer

<400> SEQUENCE: 4
attgttggct accagtttat ccaaaggg                                           28

<210> SEQ ID NO 5
<211> LENGTH: 26
<212> TYPE: DNA
<213> ORGANISM: Artificial Sequence
<220> FEATURE:
<223> OTHER INFORMATION: PCR amplification primer

<400> SEQUENCE: 5
cagaaggctg gacatataga ggaggg                                             26

<210> SEQ ID NO 6
<211> LENGTH: 27
<212> TYPE: DNA
<213> ORGANISM: Artificial Sequence
<220> FEATURE:
<223> OTHER INFORMATION: PCR amplification primer

<400> SEQUENCE: 6
attgttggct accagtttat ccaaacg                                            27

PROMOTER FOR THE PRODUCTION OF HYALURONIC ACID CONTAINING GINSENOSIDE COMPOUND K

This is a continuation application of U.S. Ser. No. 10/539,011 filed on Dec. 30, 2005 now abandoned, which is a national stage application of PCT/KR2003/001889 filed on Sep. 16, 2003, which claims priority from Korean patent application 10-2002-0084036 filed on Dec. 26, 2002, all of which are incorporated herein by reference.

FIELD OF THE INVENTION

The present invention relates to a promoter containing ginsenoside compound K for the production of hyaluronic acid. More particularly, the present invention provides a new efficacy of 20-O-β-D-glucopyranosyl-20(S)-protopanaxadiol (called "compound K"), a chief metabolite of ginseng saponin, to increase the expression of the hyaluronic acid synthase (HAS) gene in human cells and thereby to promote the production of hyaluronic acid (HA), and provides a promoter containing compound K for the production of hyaluronic acid.

BACKGROUND OF THE INVENTION

Hyaluronic acid is a nonsulfated glycosaminoglycan, linear polysaccharide with a very large molecular weight of 200,000 to 400,000 composed of repeating glucuronic acid and N-acetylglucosamine residues. Hyaluronic acid is a major structural component of the extracellular matrix and involved in water retention, maintenance of the extracellular space and storage and diffusion of cell growth factors and nutrients, as well as in cell proliferation and differentiation, and migration.

In mammals, it has been reported that 50% or more of their hyaluronic acid exists in the skin, particularly in epidermal extracellular space and dermal connective tissue, and it is synthesized by keratinocyte and fibroblasts. Further, the concentration of hyaluronic acid in human skin decreases with aging, which causes the skin to lose its elasticity and to decrease water retention (*Biochem Biophys Acta* 279, 265-275, *Carbohydr Res* 159, 127-136, *Int J Dermatol* 33, 119-122).

The human joint capsule is composed of the outer fibrous layer and the inner synovial membrane, in which synovial fluid containing hyaluronic acid and glycoprotein, functions as a joint lubricant. It has however been reported that in osteoarthritis (degenerative arthritis), the production of hyaluronic acid decreases and destruction by proteolytic enzymes is accelerated, so diminishing the concentration of hyaluronic acid in a joint. Therefore as the concentration of hyaluronic acid in a joint decreases, the joint cannot absorb or disperse shocks, so accelerating cartilage damage. Hence, hyaluronate injection was approved by the FDA in 1997 as a device for the relief of pain from osteoarthritis and has been applied thereto. However, in the end, it may be more effective to increase the biosynthesis of hyaluronic acid.

The biosynthesis of hyaluronic acid in cultured epidermal cells has been reported to be increased by various growth factors and by trans-retinoic acid, N-methylserine and the like (*Biochem. J.* 258, 919-922, *Biochem. J.* 283, 165-170, *Biochem. J* 307 817-821, *J. Biol. Chem.* 272,4787-4794, *J Invest Dermatol* 92, 326-332, *Biol Pharm Bull* 17, 361-364, *Skin Pharmacol Appl Skin Physiol* 12, 276-283). Further, there were reports that estradiol and its derivatives applied on the skin might increase the biosynthesis of hyaluronic acid (*Steroids* 16,1-3, *J Invest Dermatol* 87, 668-673, *Skin Pharmacol Appl Skin Physiol* 15, 175-183). However, the detailed mechanism for the metabolism of hyaluronic acid has not yet been fully elucidated. It has been merely known that hyaluronic acid is synthesized at the inner surface of the plasma membrane by hyaluronic acid synthase and is extruded through the membrane into the extracellular space simultaneously with the ongoing synthesis (*J. Biol. Chem.* 272, 13997-14000).

Currently, three different HAS genes have been identified in mammalian cells: HAS1, HAS2 and HAS3 which are highly homologous. In relation thereto, it was reported that HAS2 gene expression increased when an epidermal growth factor (EGF) was contained in a medium of epidermal cell line culture (*J. Biol. Chem.* 276, 20428-20435). However, studies on distribution of hyaluronic acid in cells and tissues and on various factors and enzymes related to hyaluronic acid, for example HAS or factors regulating the activity of hyaluronic acid, remain insufficient up to now.

Therefore, several continuing studies have paid attentions to the possibility of hyaluronic acid, and have extensively researched to find effective production and injection of hyaluronic acid and methods for increasing the biosynthesis of hyaluronic acid. However, obvious results are not yet known.

SUMMARY OF THE INVENTION

Under these circumstances, the present inventors researched to find an effective method for supplying hyaluronic acid into the human body. As a result thereof, we found that compound K (20-O-β-D-glucopyranosyl-20(S)-protopanaxadiol), a chief metabolite of ginsepeng saponin having immunity-increasing, tumor angiogenesis-suppressing and cancerous cell permeation-inhibiting effects, can increase the expression of gene cording hyaluronic acid synthase in human cells and thereby promote the production of hyaluronic acid in the human body. That is, the production of hyaluronic acid can be promoted by treatment with compound K, resulting in increasing the concentration of hyaluronic acid in the human body. This result suggests that compound K can be applied to various purposes utilizing the efficacy of hyaluronic acid such as skin-care uses for improvement of skin elasticity and prevention of skin drying or skin aging and pharmaceutical uses for treatment or prevention of osteoarthritis. Based on this finding, the present invention has been completed.

Therefore, an object of the present invention is to provide a new use of compound K to increase the expression of the hyaluronic acid synthase gene and thereby to promote the production of hyaluronic acid.

Another object of the present invention is to provide a promoter for the production of hyaluronic acid containing compound K as an effective ingredient.

A further object of the present invention is to provide the possibility of compound K being applied to various purposes utilizing the efficacy of hyaluronic acid such as skin-care uses for improvement of skin elasticity and prevention of skin drying or skin aging and pharmaceutical uses for treatment or prevention of osteoarthritis.

In order to accomplish the objects, the present invention provides a new efficacy of compound K, which already has been known to have efficacies such as an immunity-increasing effect, a tumor angiogenesis-suppressing effect and a cancerous cell permeation-inhibiting effect. That is to say, the invention provides a new efficacy of compound K to increase the expression of the hyaluronic acid synthase gene and thereby to promote the production of hyaluronic acid.

DETAILED DESCRIPTION OF THE INVENTION

The following is a detailed description of the present invention.

Compound K, that is, 20-O-β-D-glucopyranosyl-20(S)-protopanaxadiol represented by the following formula 1, is a chief metabolite of ginseng saponin decomposed by human intestinal bacteria (Hasegawa, H., Sung, J. H., Matsumiya. S., Uchiyama. M.,(1996) *Planta Medica* 62, 453-457).

[Formula 1]

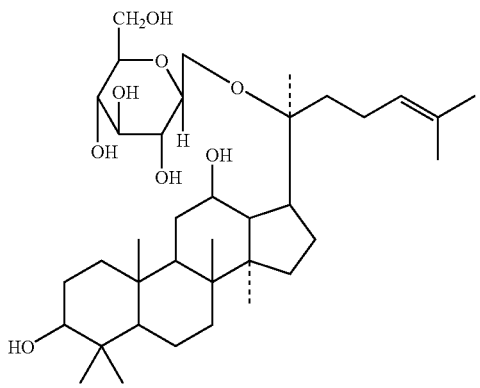

Ginsenosides and theirs derivatives derived from ginseng have the constitutions that sugar such as glucose, rhamnose, arabinose, xylose or the like is linked via ether bond to protopanaxadiol or protopanaxatriol, which are triterpenes of the dammarane series. So far, a total of a 29 types of gensenosides have been isolated from ginseng (KOREA INSAM). Shibata, in 1964, named the components of ginseng saponin as "ginsenoside", which refers to glycoside contained in ginseng. Ginsenosides are classified into ginsenoside-Ro, which is a family of oleanane saponin, and ginsenoside-Ra, -Rb1, -Rb2,-Rc, -Rd, -Re, -Rf, -Rg1, -Rg2,-Rg3 and -Rh, according to the order of movement in separating from TLC (thin-layer chromatography). Ginseng saponins have been known to exhibit different pharmacological efficacies depending on their type, number or the position of sugar bonded to aglycon. Many researches have been conducted on the pharmacological efficacy of major saponins plentifully contained in ginseng and easily isolated therefrom. However, only a few researches have been conducted on the pharmacological efficacy of minor saponins contained only in red ginseng or of saponin metabolites decomposed by human intestinal bacteria.

Among ginseng saponins, compound K, i.e. 20-O-β-D-glucopyranosyl-20(S)-protopanaxadiol, is composed of one sugar (glucose) bonded to protopanaxadiol and has been known to exhibit pharmacological efficacy in suppressing cancerous cell proliferation, suppressing tumor cell proliferation and enforcing anticancer activity of anticancer agents. In particular, extensive studies on saponin metabolites revealed that the pharmacological efficacy of ginseng saponin is due to the metabolites decomposed by human intestinal bacteria, not to the saponin itself (*Chem Pharm Bull* 38(10) 2859-2861, *Bio. Pharm. Bull* 25(6) 743-747).

The present inventors confirmed that HAS2 gene expression increased in compound K-treated human epidermal and dermal cell lines, i.e. keratinocyte cell line HaCaT and fibroblast cell line HDF. That is, treatment with compound K for 24 hours induced 3-times and 2.5-times increases in HAS2 gene expression in the cultured HaCaT and HDF cells respectively, in comparison with no treatment. Furthermore, HAS2 gene expression increased about 3-times and about 5-times during 24 hours and 48 hours incubations of HaCaT cells with treatment of 1 μM compound K, respectively. These results show that compound K has HAS2 gene expression-promoting efficacy in human cell. At the same time, it was confirmed that the concentration of hyaluronic acid in the human cell culture was increased by treatment of compound K.

In addition, the present inventors confirmed that the production of hyaluronic acid increased in the compound K-treated hairless mouse skin. When compound K was introduced to a patch and applied onto the back skin of a hairless mouse, the production of hyaluronic acid increased about 3-times in the epidermis and dennis. These results indicate that compound K has HA production-promoting efficacy in a living body.

Finally, the present inventors confirmed that wrinkle, hydration, elasticity, smoothness and brightness were improved when compound K-containing topical composition was applied onto the human skin.

Compound K employed in the present invention may be natural compound K or synthetic compound K obtained by the conventional method, but not limited thereto. Compound K may be obtained by dissolving purified saponin of ginseng in aqueous solvent such as distilled water or buffer solution, or in a mixture of the aqueous solvent and organic solvent, and then reacting with at least one of naringinase separated from *Penicillium* and pectinase separated from *Aspergillus*, but not limited thereto.

The present invention shows that compound K can increase HAS2 gene expression and promote the production of hyaluronic acid. Accordingly, compound K can be incorporated, as an effective component, into skin-care topical compositions utilizing the efficacy of hyaluronic acid. For example, it can be added into skin-care topical compositions for improvement of skin elasticity and prevention of skin drying or skin aging. Further, it can be added into medicaments for treatment or prevention of diseases, such as osteoarthritis, by administration of hyaluronic acid. However, it may not be limited thereto.

PREFERRED EMBODIMENTS OF THE INVENTION

Figure 1:
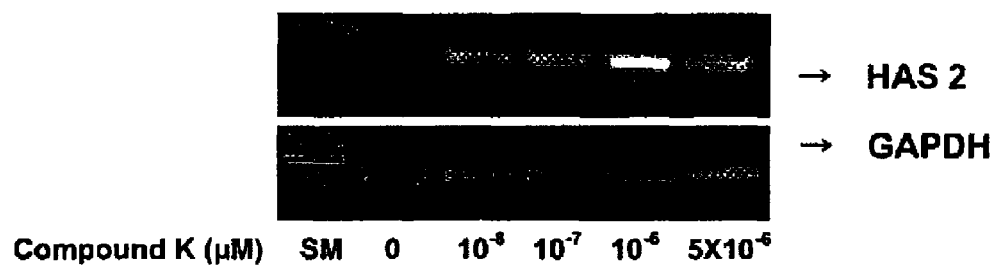
FIG. 1 is a result of quantitative RT-PCR for HAS2 gene, in order to identify HAS2 mRNA expression in keratinocyte cell line HaCaT (FIG. 1a) and fibroblast cell line HDF (FIG. 1b) after treatment with various concentrations of compound K.
Figure 1:
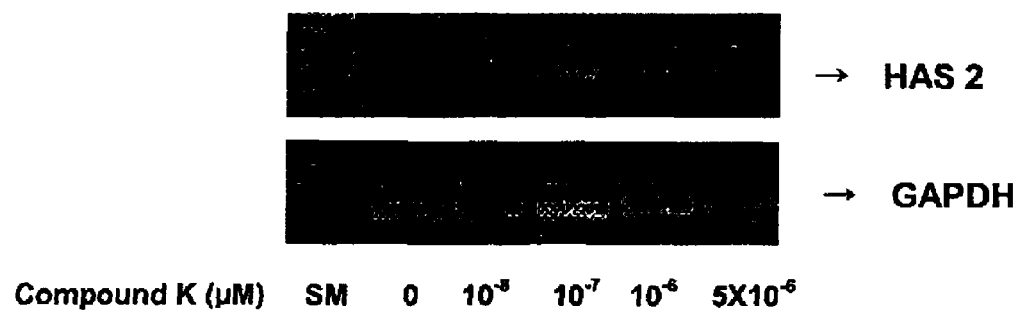

The present invention will be described in more detail by way of the following examples, which should not be considered to limit the scope of the present invention. Further, it will be apparent to one skilled in the art that various modifications and variations can be made within the scope of the present invention and without departing therefrom.

Example 1

Preparation of Compound K 10 g of ginseng extract (red ginseng, white ginseng and the root hair and leaf of ginseng) was dissolved in 2 l of citrate buffer (pH 4.0). Thereto was added 10 g of naringinase (Sigma, St. Louis, Mo.), 10 g of pectinase (Novozyme, Copenhagen, Denmark) then the mixture was cultured in 38° C. of water bath for 48 hours. After enzymetic hydrolysis was completed, the reaction mixture was extracted with 2 l of ethylacetate and then evaporated under a vacuum condition to give 2.8 g of residue. For purification of compound K, the obtained product was subjected to silica gel column chromatography, eluted with chloroform-methanol (9:1) and then with chloroform-methanol (6:1), to give 0.28 g of pure compound K.

Experimental Example 1

Effect of Compound K on HAS2 Gene Expression in Human Epidermal Cell Line HaCaT <Cell Culture>

Spontaneously immortalized human keratinocyte cell line, HaCaT, was provided by Dr. N. E. Fusenig (Deutsches Krebsforschungszentrum(DKFZ), Heidelberg, Germany) and human diploid fibroblast cell line, HDF, was provided by Dr. S. C. Park (Seoul National University, Seoul, Korea).

The cells were cultured in Dulbecco's modified Eagle's medium (DMEM) supplemented with 10% fetal bovine serum (HyClone), sodium bicarbonate (3.6 g/l) and antibiotics of streptomycin (100 µg/ml) and penicillin (100 U/ml) (Life Technologies, Inc.) at 37° C. in a humidified atmosphere containing 5% $CO_2$ and 95% air. The culture was changed with fresh medium every 3 days. On reaching the maximum cell-density, the cells were recultured at a 1:5 division ratio. 48 hours before treatment with compound K, the cells were seeded into a tissue culture flask at $1\times10^5$ cells per 75 $cm^2$ and cultured in the medium with 10% fetal bovine serum for 24 hours. Subsequently, the cells were cultured in the serum-free medium for another 24 hours and then in fresh serum-free medium supplemented with 1 to 5 µM of compound K for 3, 6, 12, 24 or 48 hours. As a control, the cells were cultured in the medium supplemented with 0.01% vehicle (dimethylsulfoxide, DMSO). In the control, no effect of DMSO on cell growth and differentiation was observed.

<Preparation of RNA>

HaCaT cells and HDF cells were washed twice with phosphate buffered saline (PBS) (Life Technologies, Inc.), and total cellular RNA was isolated with TRizol® reagent (GibcoBRL Life Technologies, Grand Island, N.Y.) according to manufacturer's instructions. RNA concentration was measured by spectrophotometry and RNA integrity was checked by agarose gel electrophoresis.

<Effect of Compound K on mRNA Synthesis of HAS1, HAS2 and HAS3, Confirmed by Quantitative Reverse Transcription-Polymerase Chain Reaction (RT-PCR) Method>

Quantitated total RNA was reverse transcribed, then RT-PCR was performed using HAS1-, HAS2- and HAS3-specific primers. In brief, 4 µg of total RNA was reverse transcribed in 25 µl of reaction mixture containing 2.5 U/µl Superscript II reverse transcriptase (Invitrogen, Carlsbad, Calif.), 1 U/µg RNase inhibitor, 5 mM $MgCl_2$, 50 mM KCl, 10 mM Tris-HCl (pH8.3), 2.5 µM oligo(dT) primers and 1 mM dNTPs. The reaction mixture was gently incubated at 42° C. for 60 min, to be subjected to reverse transcription. Then, the reverse transcriptase was inactivated by heating at 85° C. for 5 min.

Figure 2:
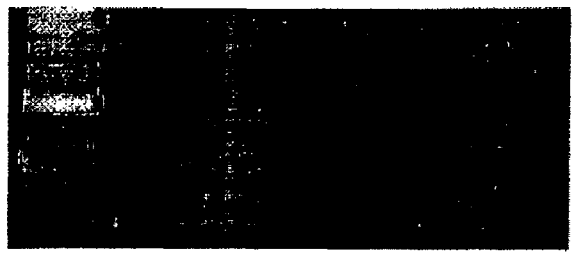
FIG. 2 is a result of quantitative RT-PCR for HAS1, HAS2 and HAS3 genes, in order to identify HAS mRNA expression in HaCaT cells after treatment with compound K for various time periods.
Figure 2:
Figure 2:
Figure 2:

Subsequently, 5 µl of the resulting mixture was subjected to PCR. Each PCR was performed using Perkin-Elmer Cycler 9600 (Perkin-Elmer Applied Biosystems, Foster, Calif.) in 50 µl of reaction mixture containing 0.04 U/µl AmpliTaq™ DNA polymerase (Perkin Elmer, Shelton, Conn.), 50 mM Tris (pH8.3), 0.25 mg/ml BSA, 3 mM $MgCl_2$, 0.25 mM dNTPs and 0.25 µM sense or antisense PCR primers (Table 1) under a PCR thermal profile consisting of denaturation at 95 C for 5 min prior to the initial cycle and 25~35 cycles of 45 sec at 95° C., 45 sec for 60° C. and 1 min at 72° C. The PCR products were electrophoresed through agarose gels and visualized with ethidium bromide staining. The results are shown in FIG. 1 and FIG. 2. GAPDH is a criterion for standardization of the amplified products.

TABLE 1

Sequences of HAS1-, HAS2- and HAS3-specific primers for quantitative RT-PCR

| Primers | | Sequences |
|---|---|---|
| HAS1 | Forward | 5'-ACCATCGCCTTCGCCCTGCTCATCC-3' |
| | Reverse | 5'-CCCGCTCCACATTGAAGGCTACCCA-3' |
| HAS2 | Forward | 5'-TTTCTTTATGTGACTCATCTGTCTCACCGG-3' |
| | Reverse | 5'-ATTGTTGGCTACCAGTTTATCCAAAGGG-3' |
| HAS3 | Forward | 5'-CAGAAGGCTGGACATATAGAGGAGGG-3' |
| | Reverse | 5'-ATTGTTGGCTACCAGTTTATCCAAACG-3' |

FIG. 1 is a result of quantitative RT-PCR for HAS2 gene, in order to identify HAS mRNA expression in keratinocyte cell line HaCaT (FIG. 1a) and fibroblast cell line HDF (FIG. 1b) after treatment with various concentrations of compound K, and shows the effect of the compound K on HAS2 mRNA level. In this experiment, HAS2 mRNA was detected in a small amount in the control, but increased 3-times and 2.5-times in compound K-treated HaCaT cells and HDF cells, respectively.

FIG. 2 shows the effect of compound K on HAS1, HAS2 and HAS3 transcription in the HaCaT cells. HaCaT cells were cultured for 24 or 48 hours in the medium with 0 or 1 µM compound K added thereto, then total RNA was isolated therefrom. Total RNA was reverse transcribed and amplified for 30 PCR cycles. As a result, HAS2 transcription increased about 3-times and about 5-times during 24 hr and 48 hours incubation of HaCaT cells treated with compound K, respectively. However, compound K did not influence the HAS1 and HAS3 mRNA levels detected in small amount.

Experimental Example 2

Effect of Compound K on Production of Hyaluronic Acid in Human Epidermal and Dermal Cell Lines HaCaT and HDF cells were washed with PBS then fixed in a fixative with 2% paraformaldehyde(v/v) and 0.5% glutaraldehyde(v/v) at room temperature for 20 min. After fixation, the cells were washed three times for 2 min each with 0.1 M sodium phosphate buffer (pH7.4), then blocked in 1% bovine serum albumin (w/v) containing 0.1% Triton X-100 (v/v) in the same buffer at room temperature for 30 min. Hyaluronan staining was carried out with a specific probe of biotinylated hyaluronan binding protein (bHABP) (Seikagaku, Tokyo, Japan). The bHABP probe, diluted to 5 μg/ml in 3% bovine serum albumin (w/v), was added to the fixed cells and was incubated overnight at 4° C. After washing, avidin-fluorescein isothocyanate (FITC) was added. Images were analyzed with fluorescent microscope and are shown in FIG. 3.

Figure 3:
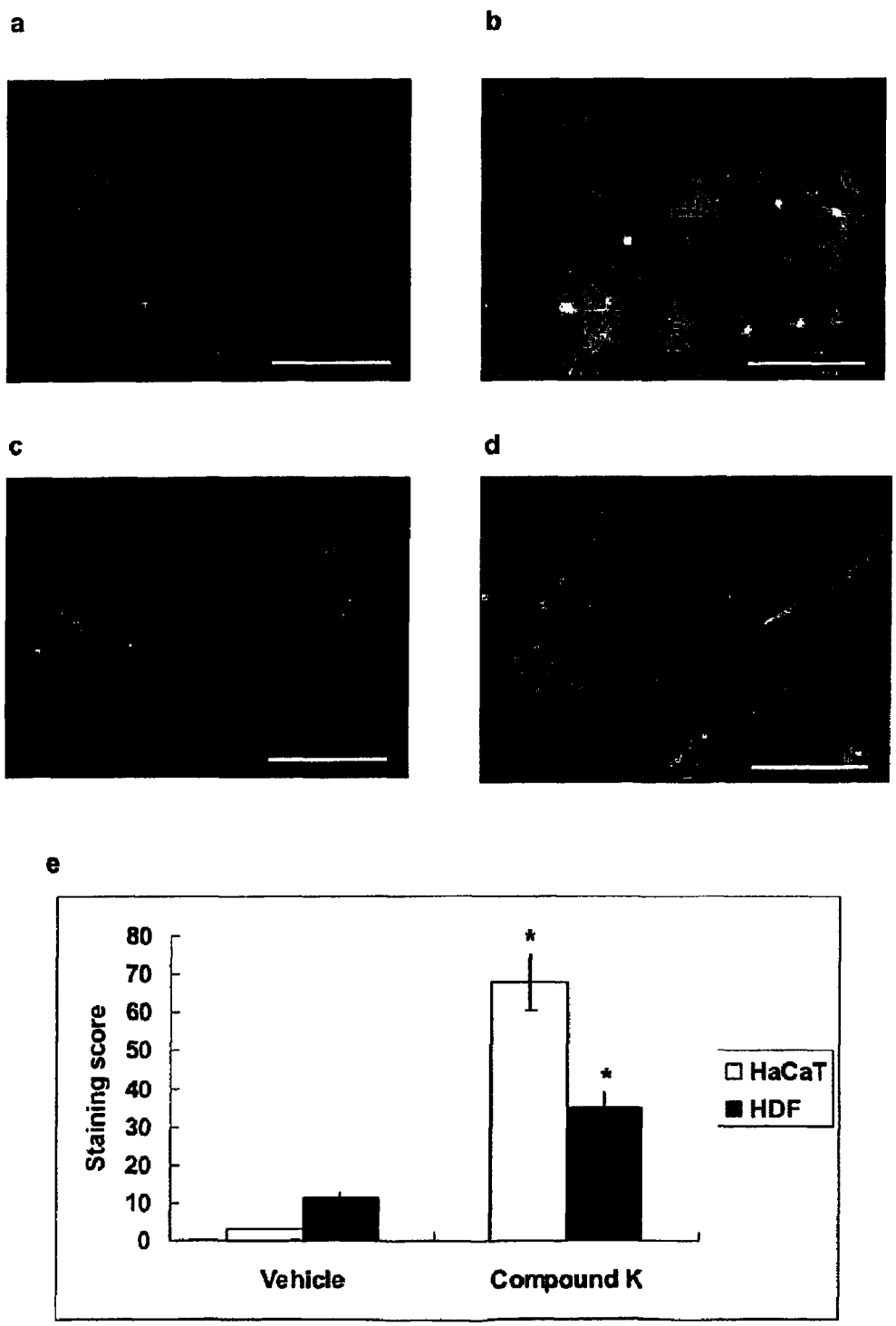
FIG. 3 shows the effect of compound K on the distribution of hyaluronic acid in the cultured HaCaT and HDF cells. After treatment with 1 μM of compound K, the increased production of hyaluronic acid was confirmed by the immunocytochemical method and then the result was quantitated.

FIG. 3 shows the effect of compound K on the distribution of hyaluronic acid in the cultured HaCaT and HDF cells. HaCaT cells (FIG. 3a, FIG. 3b) and HDF cells (FIG. 3c, FIG. 3d) were cultured in the presence of 1 μM compound K (FIG. 3b, FIG. 3d) or in the absence of compound K (FIG. 3a, FIG. 3c).

Experimental Example 3

Effect of Compound K on the Production of Hyaluronic Acid in Hairless Mouse Skin <Hairless Mouse and its Treatment>

Male albino Hos:hr-1 mice, 30 weeks old, were purchased from Biogenomics (Seoul, Korea) and had unrestricted access to standard rodent chow and water. After one week of acclimation under controlled conditions of 24±2° C. and 55±10% humidity, 200 μl of 1%(w/v) compound K solution in the vehicle (1,3-BG:ethanol-7:3) was topically applied onto the back of the mouse two times for 2 days. 24 hours after the final administration, each skin sample was collected.

<Immunohistochemical Staining with Hyaluronan Binding Protein on the Compound K-Treated Skin>

Hyaluronan staining was carried out with bHABP(Seikagaku). Each skin sample was fixed with 2% formaldehyde and 0.5% glutaraldehyde in PBS, embedded and sectioned. After deparaffinization, sections were incubated in 0.3% $H_2O_2$ in methanol at room temperature for 30 min, washed with PBS, then blocked in 1% bovine serum albumin. Subsequently the sections were incubated in 5 mg/ml bHABP in PBS at 4° C. then, after washing, incubated with streptoavidin-peroxidase, diluted to 1/300 in PBS at room temperature, for 30 min. After washing, each slide was reacted with 3,3'-diaminobenzidine tetrahydrochloride(DAB) at room temperature for 5 min. After washing with distilled water, staining was carried out with Mayer's hematoxylin.

<Analysis of Image and Data Obtained by Immunohistochemical Staining>

Stained slides were quantitatively characterized via digital image analysis using ImagePro-Plus (Media Cybernetics, Silver Spring, Md.). Images were captured through an Olympus BH-2 microscope fitted with a MicroImage video camera (Boyertown, Pa.). Parameters, such as total area, total stained area, and intensity of stain, were taken from a series of 10 random images on several slides to obtain a mean value for statistical comparison. Staining score is determined by the following formula 1:

$$\text{Intensity of stain} \times (\text{total stained area/total area}) \quad \text{Equation 1}$$

One-way ANOVA with post-hog Duncan test was performed using SigmaStat (SPSS Inc., Chicago, Ill.). Data were expressed as the mean±SEM. Significance was considered at p<0.05.

Figure 4:
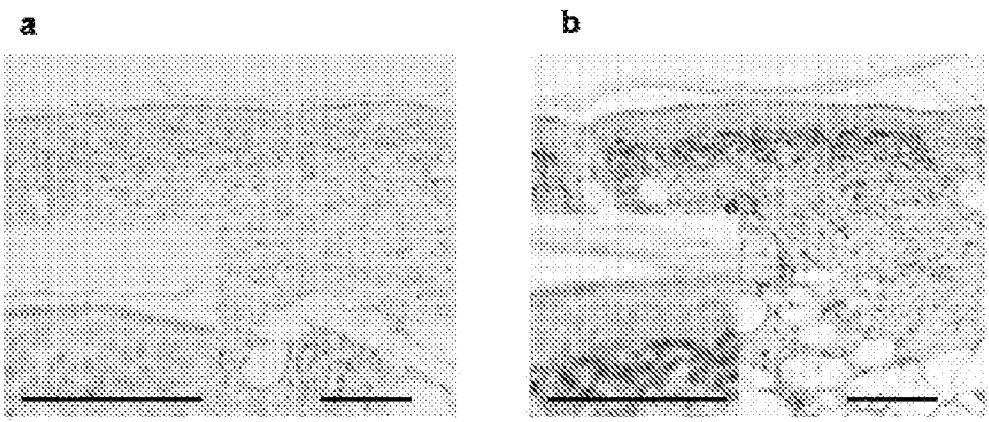
FIG. 4 shows the increased production of hyaluronic acid in the compound K-treated back skin of the hairless mouse, confirmed by immunohistochemical staining.
Figure 4:
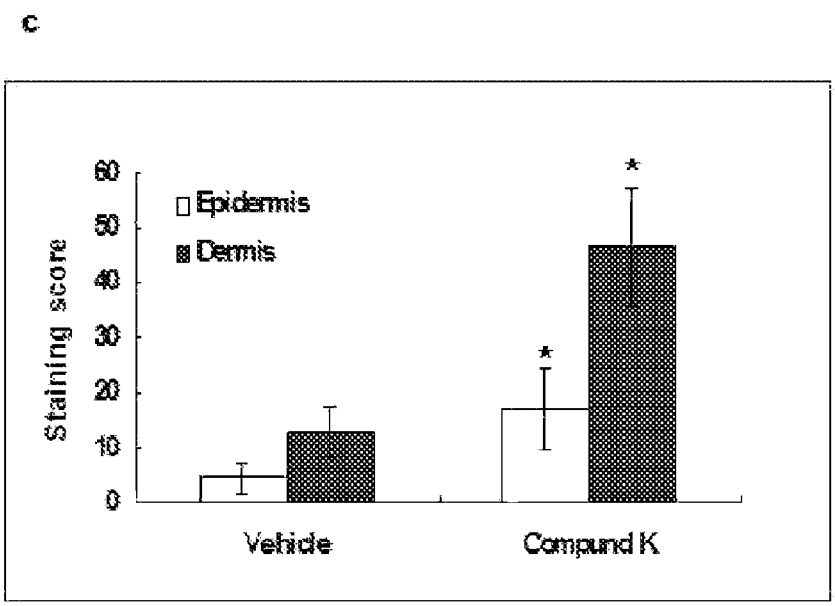
Figure 4:
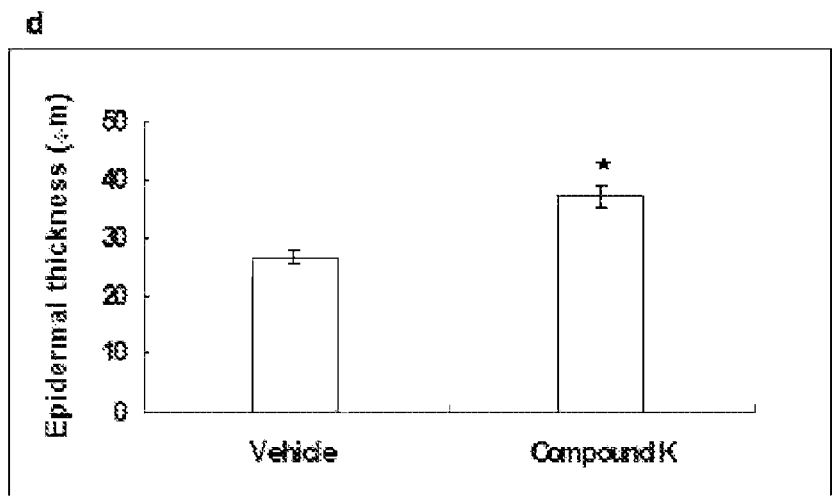

FIG. 4 shows hyaluronic acid widely deposited in the epidermis and dermis. It shows that hyaluronic acid significantly increased in compound K-treated hairless mouse skin. As shown in FIG. 4a and FIG. 4b, the amount of hyaluronic acid increased predominantly in the extracellular papillary dermis and in the viable epidermis of the compound K-treated murine skin. FIG. 4c is a result of quantitative image analysis, showing that the amount of HA increased 3-folds in epidermis and dermis of the compound K-treated murine skin, respectively, as compared with the untreated skin. (p<0.05).

The above results confirm that treatment of the skin cells with compound K increases the expression of hyaluronic acid synthase, HAS2 gene, resulting in promotion of the production of hyaluronic acid in the epidermis and dermis of the skin.

Experimental Example 4

Evaluation for Skin-Care Efficacy

<Topical Application>

In order to evaluate the efficacy of the cosmetic composition containing compound K, a clinical trial was conducted with forty-nine (49) healthy Korean females aged from 31 to 37 years and having facial wrinkle and fine wrinkle. They were divided into three groups by skin type: normal skin, dry skin and combination skin and used two kinds of oily-water emulsions containing 0.03% compound K or none. Before the trial, all the volunteers were evaluated for facial wrinkle and fine wrinkle with a global photodamage score. All the scores were obtained before use and 4, 8 and 12 weeks after use. Each volunteer applied test samples onto the facial skin twice per day (morning and evening) at their homes, and particularly onto the wrinkles of the eye rims.

<Efficacy Evaluation>

Skin-care efficacies such as facial wrinkle, fine wrinkle, hydration, elasticity, smoothness, roughness and brightness were evaluated by the volunteers and skin expert inspectors. Difference before and after using topical samples and improvement were determined by photometry evaluation with Camscope® (model DCS-105) and by image analysis of silicon replica with Skin-Visiometer SV 600 (Courage & Khazaka, Germany).

Figure 5:
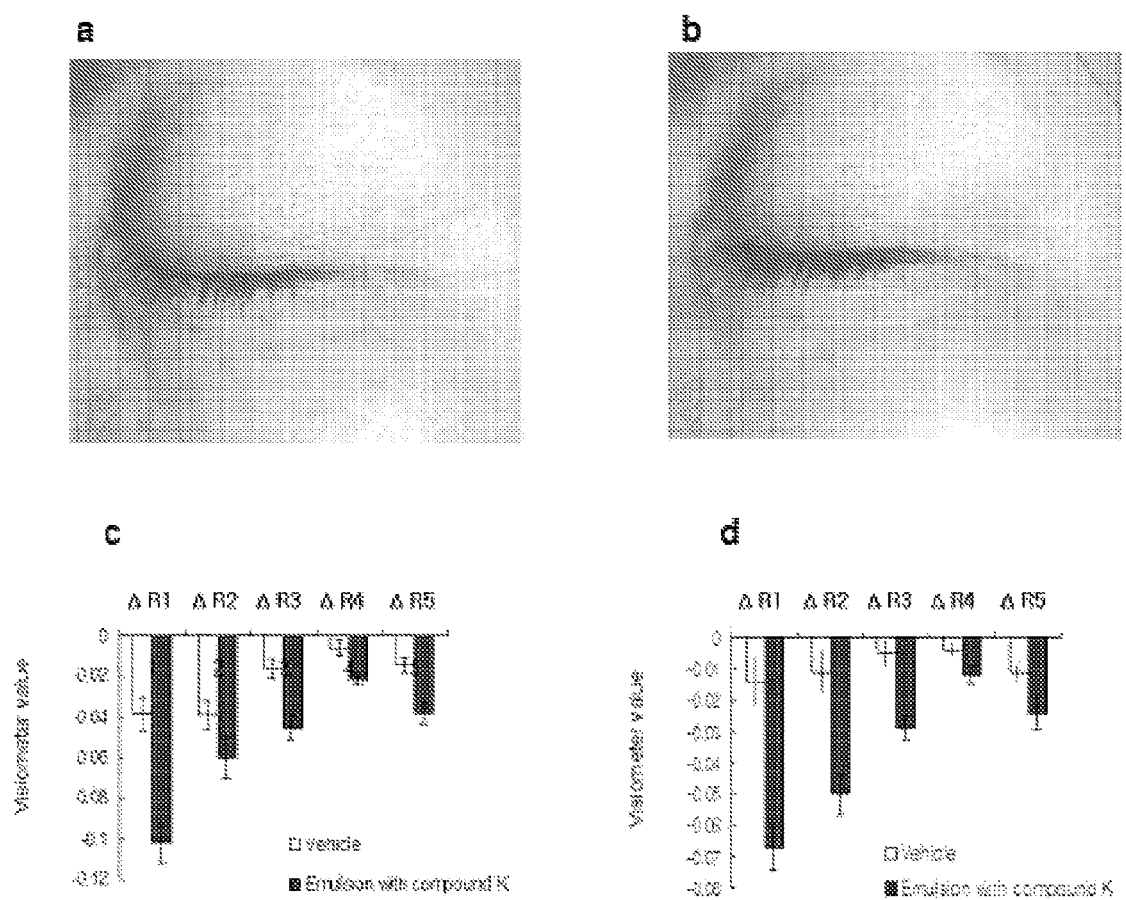
FIG. 5 shows morphological changes in human skin by treatment with the compound K-containing topical composition.

FIG. 5 shows a result of evaluation with global photodamage score conducted by skin expert inspectors. In a comparison of initial values measured before use and values measured after 12 weeks of use of the emulsions with or without compound K as a control, it was found that compound K induced statistically significant decrease in facial wrinkle and fine wrinkle (FIG. 5a). In the clinical trial, 76% of volunteers after 8 weeks of use and 92% of volunteers after 12 weeks of use gave positive and affirmative estimate (FIG. 5b).

In skin replica analysis, it was found that total wrinkle decreased statistically significantly after 8 weeks of use. 92% of volunteers answered improvement in skin smoothness; 68% answered improvement in skin brightness; 68% answered improvement in skin elasticity; and 94% answered improvement in skin roughness. 88% of volunteers answered increase in skin moisturizing capacity.

INDUSTRIAL APPLICATION OF THE INVENTION

As above described, compound K, a chief metabolite of ginseng saponin, can increase expression of gene coding hyaluronic acid synthase 2 and thereby activate the production of hyaluronic acid in a living body. Therefore, compound K can be used for effective prevention of skin elasticity reduction, water retention reduction and skin aging. Further, it can be effectively used for prevention and treatment of osteoarthritis, utilizing hyaluronic acid for remedial value.

The invention claimed is:

1. A method for reducing wrinkles in the skin of a human comprising applying an effective amount of a composition comprising isolated 20-O-b-D-glucopyranosyl-20(S)-protopanaxadiol represented by the following Formula 1, to the skin of the human, wherein the composition is an oily-water emulsion:

Formula 1

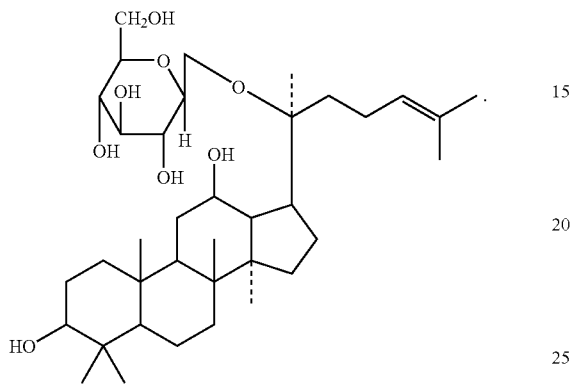

2. The method of claim 1, wherein the composition comprises 20-O-b-D-glucopyranosyl-20(S)-protopanaxadiol in an amount of 0.03 wt % based on the total weight of the composition.

* * * * *